(12) United States Patent
Liggett et al.

(10) Patent No.: US 8,061,214 B2
(45) Date of Patent: Nov. 22, 2011

(54) BIAXIAL STRESS, SHEER, PERMEABILITY, AND PEEL TEST METHOD AND MACHINE TO CONDUCT THE SAME

(75) Inventors: Paul E. Liggett, Wooster, OH (US); Dennis L. Carter, Hudson, OH (US); Nicholas L. Barnes, Wellington, OH (US); James I. Mascolino, North Canton, OH (US); Anthony L. Dunne, Hudson, OH (US); Aaron C. Graham, Mogadore, OH (US)

(73) Assignee: Lockheed Martin Corporation, Akron, OH (US)

( * ) Notice: Subject to any disclaimer, the term of this patent is extended or adjusted under 35 U.S.C. 154(b) by 867 days.

(21) Appl. No.: 12/117,016

(22) Filed: May 8, 2008

(65) Prior Publication Data

US 2011/0174056 A1 Jul. 21, 2011

(51) Int. Cl.
*G01N 3/00* (2006.01)
(52) U.S. Cl. ........................................... 73/788
(58) Field of Classification Search .................... 73/788, 73/831, 849, 856, 760–761, 862.632
See application file for complete search history.

(56) References Cited

U.S. PATENT DOCUMENTS

| 3,580,065 | A | | 5/1971 | Strittmater et al. |
| 4,501,154 | A | | 2/1985 | Mori |
| 4,612,805 | A | | 9/1986 | Bruce |
| 4,970,895 | A | * | 11/1990 | Houghton et al. ............... 73/159 |
| 6,074,722 | A | | 6/2000 | Cuccias |
| 6,478,264 | B1 | | 11/2002 | Nelson |
| 6,538,725 | B2 | | 3/2003 | Potyrailo |
| 6,860,156 | B1 | | 3/2005 | Cavallaro |
| 6,979,479 | B2 | | 12/2005 | Lavan |
| 7,798,014 | B2 | * | 9/2010 | Ferguson et al. ............... 73/831 |
| 7,958,790 | B2 | * | 6/2011 | Gleghorn et al. ........ 73/862.632 |
| 2002/0170360 | A1 | * | 11/2002 | Anand et al. .................... 73/849 |
| 2009/0007692 | A1 | * | 1/2009 | Ferguson et al. ............... 73/831 |

* cited by examiner

*Primary Examiner* — Jewel V Thompson
(74) *Attorney, Agent, or Firm* — Daniel J. Schlue; Roetzel & Andress

(57) ABSTRACT

The subject invention relates to an apparatus and process for testing various parameters and properties of high strength flexible, fabric laminates. In particular, the apparatus comprises a machine using individually controlled loads to test various material parameters.

30 Claims, 4 Drawing Sheets

BIAXIAL STRESS, SHEER, PERMEABILITY, AND PEEL TEST METHOD AND MACHINE TO CONDUCT THE SAME

STATEMENT OF GOVERNMENT INTEREST

The government may have a paid-up license in this invention and the right in limited circumstances to require the patent owner to license others on reasonable terms as provided for by the terms of Contract No. HQ0006-06-C-0001 awarded by the Missile Defense Agency—Department of Defense.

FIELD OF THE INVENTION

The present invention relates to a process and apparatus for testing flexible, fabric laminate materials. More specifically, the invention relates to a process and apparatus to test flexible, fabric laminate materials under various conditions of stress.

BACKGROUND OF THE INVENTION

Plain-woven fabrics are widely utilized as structural materials for many applications including inflated structures, fabric roofing, and large canopies, among others. In these capacities, the materials are primarily affected by variations in weather, i.e., temperature changes, precipitation, and wind, though stress due to weight and pressure is also a concern. Therefore, while such structures are designed to be lightweight and pliable, they must also exhibit superior strength and durability.

These materials may also find application in lighter-than-air vehicles, such as aerostats, balloons, and airships, including blimps and dirigibles, which are used in many different applications, such as near large sporting, entertainment or cultural events, or in large metropolitan areas to provide advertising or to provide high level coverage of the events. Lighter-than-air vehicles are also used in high altitude applications, for the purpose of weather monitoring and/or military surveillance. In such instances, the higher a vehicle can operate translates into an increased amount of area that can be viewed for surveillance purposes and/or weather monitoring. Additionally, lighter-than-air vehicles that possess the ability to operate at altitudes above 50,000 feet are not a hazard to commercial air traffic, are more difficult to detect and/or destroy, can be used for the surveillance of wide areas, and thus can provide a strategic and/or economic, as well as providing a means to relay communications.

Of particular interest herein are structural materials for use as the hull material in lighter-than-air vehicles, though the apparatus and method of using the same disclosed herein will find application in testing materials for any of the foregoing uses. For example, typical high altitude lighter-than-air vehicles are made from flexible, fabric laminates including lightweight materials that withstand a wide range of temperature variation and daily expansion and contraction due to such temperature variations, ozone degradation, and exposure to ultraviolet light. Materials employed for more conventional uses may experience these same conditions, though generally to a lesser extreme.

Many uses of these materials result in localized stresses in addition to overall stress and strain. For example, if the material bears logo or identification lettering, as in the case of advertising balloons or dirigibles, the logo or lettering may generate localized heat accumulation. Other potential localized stress areas are seams where panels of flexible, fabric laminate are joined together using structural seam tape to form larger structures. The area along the edge of the seams is subject to greater stress, due to the transition in stiffness of the fabric laminate to the seam area, resulting in increased potential for material failure.

In light of the environmental extremes and other stresses experienced by materials used for any of the foregoing applications, and particularly those experienced by materials used for lighter-than-air vehicle application, the materials of choice for such applications are typically high strength materials. For example, U.S. Pat. No. 6,074,722 to Cuccias teaches a fabric laminate made of a layer of polyurethane resin used to bond layers of high strength liquid crystal thermotropic (melt spun) polyester (VECTRAN®), aromatic polyaramide (KEVLAR®), or polyester (DACRON®) fiber woven yarn to a polyvinyl fluoride (TEDLAR® or MYLAR®) layer, and having an outer layer of a material that is resistant to degradation by ultra violet radiation. U.S. Pat. No. 6,979,479 teaches a laminate of a liquid crystal polymer fiber yarn layer (VECTRAN®) as an interior surface, an adhesive layer, a polyimide layer, and a polyvinylidene fluoride (PVDF) layer which forms the exterior surface.

In these materials, the various layers function as a gas barrier, to retain helium or hydrogen, and/or to provide protection from degradation caused by, for example, ozone or ultraviolet radiation. The flexible, fabric laminate may further include a thin metallic coating to provide a means for passive thermal management, reduce helium permeation, minimize the affects of lightening strikes, and provide a means for uniform static electricity distribution over the hull surface.

As noted above, the flexible, fabric laminate materials experience a variety of extreme environmental parameters. In addition, stress and strain is compounded by the need to use materials that minimize the weight of the vehicle or device. For example, a reduction in the quantity of laminating adhesive, opening the fabric weave to leave more space between fibers or yarns and using the smaller, lower denier yarn can help to reduce the weight but may also reduce the strength and increase local stress concentrations in a fabric laminate. Clearly, there is a fine balance between the necessity to use a lightweight material, yet use a material that can withstand extreme operating conditions.

In light of the foregoing, it is imperative that the properties of a flexible, fabric laminate and its constituent materials be known in as detailed a manner as possible in order to predict potential use limitations, up to the point of material failure. Knowledge of the strength and property limitations of flexible, fabric laminate materials, and particularly of lightweight, high strength fabric laminate materials, will allow for use of the materials within the confines of certain system designs.

Known machines and apparatuses that are used to test material strengths and property limitations of the type discussed hereinabove are limited to devices capable only of creating uniaxial and/or symmetrical biaxial stress. Typically, a tensile test machine is used to generate uniaxial forces to evaluate the strength and performance of materials. However, for inflated structures, such as an airship, aerostat, or blimp, the stresses in the hull material due to the inflation pressure are biaxial and unlikely to be equal. For example, the stress in the hoop or circumferential direction is two times the stress in the longitudinal or axial direction. To characterize and evaluate the actual performance of airship hull fabric laminates, it is necessary to test them while under simultaneous, unequal, independent, biaxial stress. If the lighter-than-air vehicle is spherical, such as a balloon, the stresses are generally equal in all directions.

Certain machines are capable of testing in-plane shear strength as well; however, machines with this capability do not create independent biaxial stress. While machines with the ability to apply symmetric biaxial force can simulate operational stresses to a certain degree, they fail to provide a means to accurately test a fabric laminate under more realistic applied stress conditions that the material will experience in use, particularly, the application of sheer stress simultaneously with independently varied biaxial stresses.

As can be seen from the foregoing, what is needed is an apparatus capable of generating biaxial loads, independently of each other, to assess biaxial stress and strain, and to further test and evaluate in-plane sheer. In addition, such an apparatus that also assesses gas permeability, gas barrier film delamination and other such parameters while simultaneously subjected to biaxial loads and in-plane shear is needed to more accurately predict the performance of flexible, fabric laminate materials under extreme conditions.

SUMMARY OF THE INVENTION

In one aspect the invention relates to an apparatus for testing performance parameters of a material, the apparatus comprising multiple load-generating mechanisms, each such mechanism being operable independent of each other such mechanism In another aspect, the invention relates to a method for testing the performance parameters of a material under stress comprising: providing a material to be tested; positioning the material in a testing apparatus; simultaneously applying at least two forces to the material at two different locations on the material; measuring the amount of force applied to the material; and using the measured force to predict the failure point of the material under stress.

In still another aspect of the invention, the invention relates to an apparatus for testing performance parameters of a material, the apparatus comprising multiple load-generating mechanisms, each such mechanism being operable independent of each other such mechanism, wherein the performance parameters are tested by evaluating at least two of stress, strain, sheer, cyclic loading, gas permeability, and ply or film separation simultaneously, and to a method for using the same to predict the failure point of a flexible, fabric laminate.

DETAILED DESCRIPTION OF THE DRAWINGS

A more complete understanding of the invention and many of the various advantages thereof will be readily appreciated as the same becomes better understood by reference to the following detailed description when considered in conjunction with the accompanying drawings wherein.

DETAILED DESCRIPTION OF THE INVENTION

Figure 1:
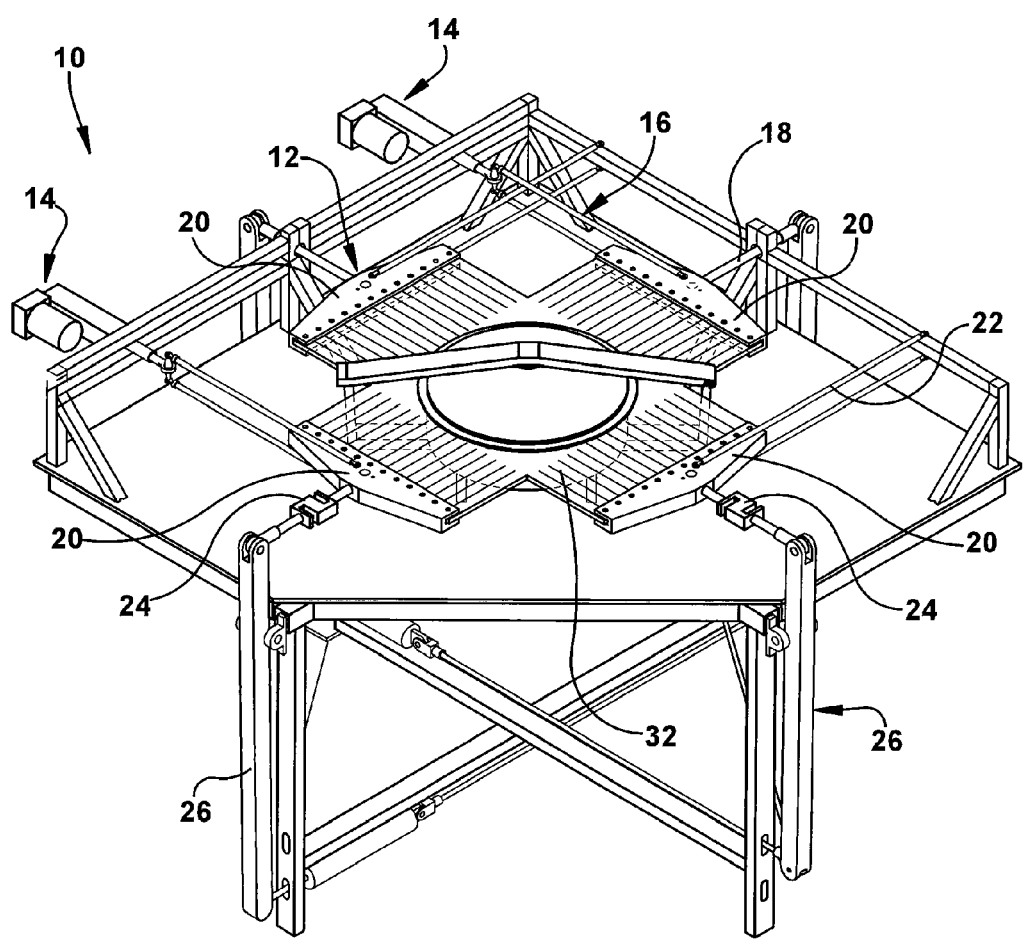
FIG. 1 is a diagram of a biaxial and sheer loading machine according to the invention.

The subject invention relates to an apparatus and process for testing various parameters and properties of flexible, fabric laminate materials. In particular, the apparatus comprises a machine using individually controlled biaxial loads to test various material parameters. For example, biaxial strength of a material may be tested. "Biaxial" as used herein refers to a load or state of stress in two orthogonal directions, which may be the same load, but may also be different loads.

In one aspect, the invention disclosed herein provides an apparatus capable of applying individually, either uniaxial or biaxial controlled loads, simultaneously, to test various material parameters.

In another aspect of the invention, an apparatus is provided that can assess the permeability of a flexible, fabric laminate material, with regard to the permeation of, for example, nitrogen, air, helium or hydrogen while the material is subjected to various, simultaneous combinations of independent biaxial, in plane shear, cyclic and pressure loading conditions. In yet another aspect of the invention, an apparatus is provided that assesses the capability of a flexible, fabric laminate material to resist delamination or peeling while subjected to the various, simultaneous loading conditions.

In still another aspect, the apparatus of the subject invention applies stress in two principle directions. In addition, the apparatus has the capability of applying in-plane sheer by additionally applying two balanced, opposite loads to create a sheering moment in a flexible, fabric laminate material already experiencing biaxial stress. This stress situation can be equated to that experienced by, for example, an airship, the skin of which will experience all of these types of loads to one degree or another.

As is stated hereinabove, known biaxial testing machines are capable of testing individual loads. However, known machines that also test sheer do not have this capability. This means that the machine can only load the flexible, fabric laminate material being evaluated in a 1:1 ratio in two orthogonal directions. The apparatus and system provided herein, however, is not so limited, and instead provides for individual loading of the flexible, fabric laminate material in any ratio desired, and for the addition of in-plane sheer, all being tested simultaneously. This is important to assessing actual in-use performance parameters where, for example, an airship may experience load ratios of from 1:1, mainly at the ends of the airship where the geometry is most like a sphere, to 2:1, mainly in the center of the airship where the geometry is most like a cylinder. With traditional testing machines, a different machine would be needed to test this central load ratio, for example a cylinder tester, than one would use to test the end region load ratio.

One advantage of the method and system design of this aspect of the invention is that the load ratio may be varied to fit any stress state, without the necessity of using multiple machines. This capability provides more accurate data for assessing the overall qualification of a certain material for use in a particular application. More critically, a flexible, fabric laminate material's failure points can be assessed, thus providing valuable data for the prediction of use limits. The fabric or material strain parameters may be measured using, for example, available techniques including but not limited to photogrammatery strain gauges, extensometers, and others.

FIG. 1 is a diagram of an apparatus in keeping with the invention. In this figure, apparatus 10 is capable of measuring biaxial stress, in-plane sheer, permeability, and peel. Pivot interface 12 provides a pivoting joint between the load link and clamp to provide necessary flexibility to allow for fabric movement, though it is important that the material or fabric not experience wrinkling during the testing. Wrinkling of the material can cause stress concentrations that would not likely occur in the fabric during use, thus making it difficult to determine and evaluate the true stress state of the material.

The apparatus according to the invention is constructed to allow movement of the material during testing, i.e., the material is not intended to remain square during sheer loading, to maintain an even material load.

Sheer loading elements 14 provide a means for generating the force, which will be converted to sheer loading of the material sample. This loading is generally applied as a lesser load in comparison to the biaxial loads applied. For example, for high strength flexible, fabric laminate materials, the shear load may be a factor of 10 to 20 less than in the main, biaxial load direction.

Active shear linkages 16 provide a means for measuring the load that is transferred to the clamps during testing and evaluation. The passive primary load linkages 18 provide a linkage to transfer reacted loads from the active links into the clamping mechanism 20.

Fabric clamps 20 each have 2 plates, for example comprised of metal, though other plate materials may be used, between which the fabric test material 32 is clamped. The clamps shown in FIG. 1 are placed directly across from each other, one on each side of the apparatus. Though the clamps are likely always to be placed in symmetrical pairs, it is envisioned that spacing between different pairs of clamps may vary depending on the tests to be performed. Clamping the material or fabric in this manner provides stability in both the pulling and sheer directions. The cruciform shape of the fabric test material 32, which includes multiple, parallel slits cut in cruciform arms, allows attachment to the clamping mechanism 20 and minimizes distortion and stress concentrations in the central test area due to independent loading in the diametrically orthogonal directions. Fixed sheer linkages 22 provide the stability necessary to accomplish sheer loading. It is noted that any linkage specified herein as passive could be replaced with an actuator and a set of active linkages.

Active primary load linkages 24 are instrumented linkages. By "instrumented" is meant that the linkages include load cells. The load cells are placed in-line with the linkage and operate to convert the force applied or generated into an electrical signal, which can then be gathered by a suitable mechanism for doing so and converted into the desired stress measurement.

The primary loading elements, or force multiplication arms, 26 provide the force, which loads the orthogonal directions of the material. Shown in FIG. 1 is an actuator acting through a load multiplying lever. The load could also be applied directly or indirectly through the use of, for example, an electric actuator, a pneumatic cylinder or cylinders, a hydraulic cylinder or cylinders, screw mechanisms and/or weights.

Figure 2:
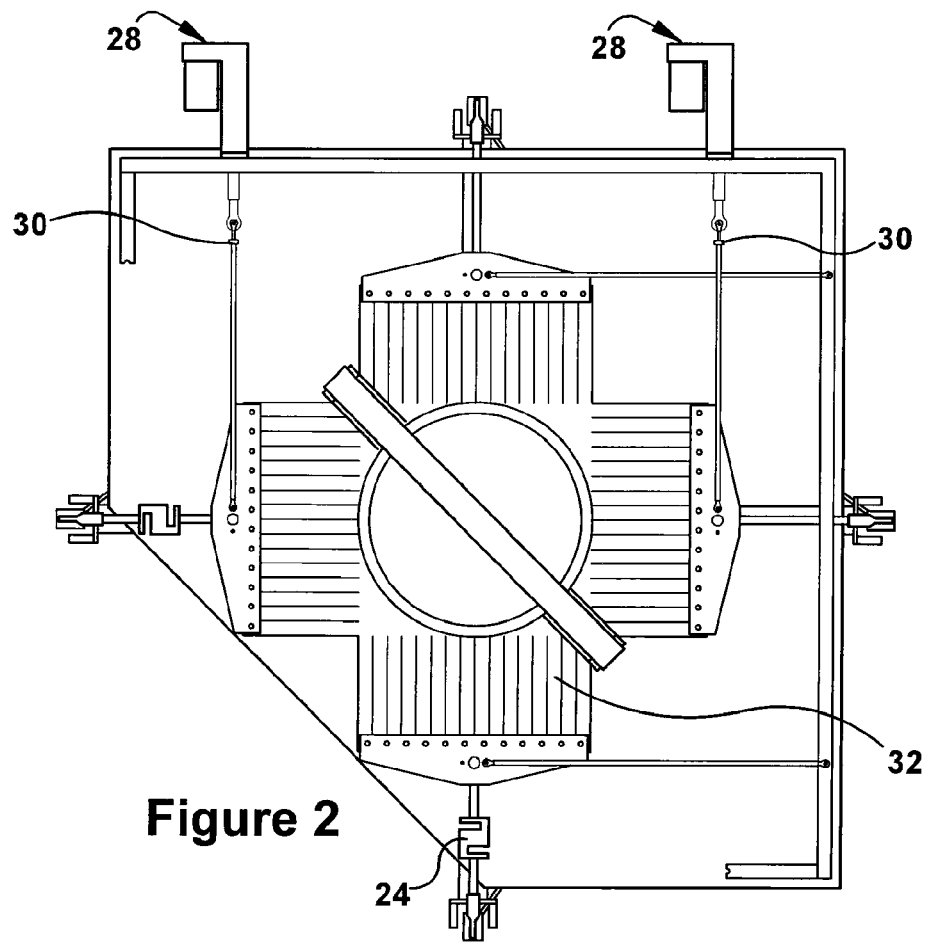
FIG. 2 is a top view of the biaxial and sheer loading machine shown in FIG. 1 with a gas permeability apparatus.

FIG. 2 is a top view of the apparatus shown in FIG. 1, illustrating shear load actuators 28 and shear load cells 30. In FIG. 1, the test area of the material 32 is shown to be placed in the center of the apparatus. Main load cell, or active primary load linkage, 24 is also shown. This cell 34, as compared to the shear load cells 30, measures the force that is applied to the fabric through the clamp. This measurement can then be converted to an applied material stress.

Figure 3:
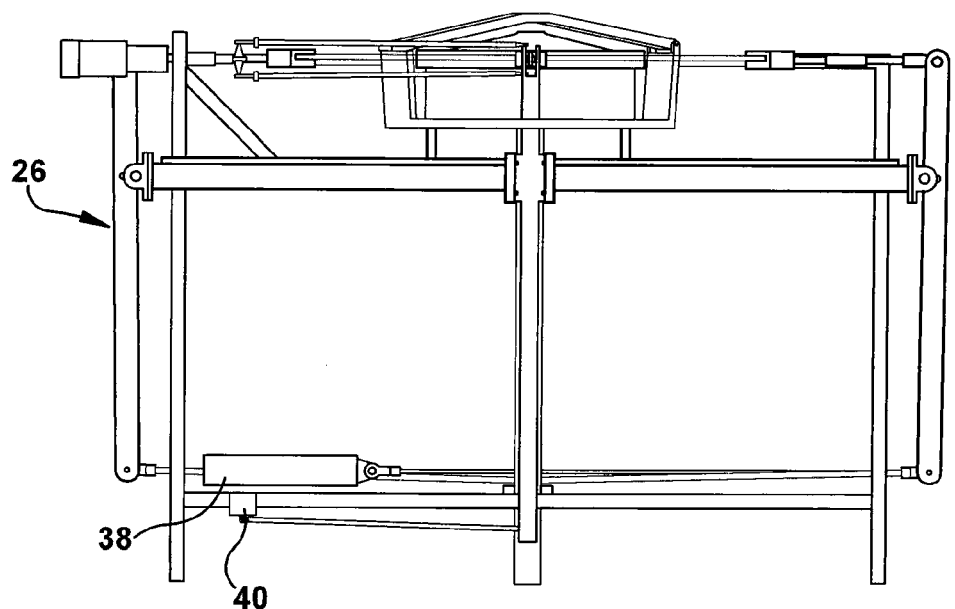
FIG. 3 is a side view diagram of the biaxial and sheer loading machine shown in FIG. 1.

FIG. 3 is a side view of the apparatus shown in FIG. 1, better illustrating force multiplication arm 26. The apparatus shown in FIG. 1 has 4 such force multiplication arms. The force multiplication arms cooperate to generate the desired simulated stress and strain. For example, the actuator side may be longer than the clamp side, resulting in an increased force being applied on the short side or clamp side. Main loading actuators 38 are located near the lower portion of the apparatus in the FIG. 1 design, though this placement is not critical. FIG. 3 further illustrates a centering link system 40.

This system operates to ensure that the main load arms 26 remain centered in the test stand or apparatus during a testing cycle. Alternatively, additional actuators could be used. Further, an active control system could be applied to maintain the stability of the apparatus.

Figure 4:
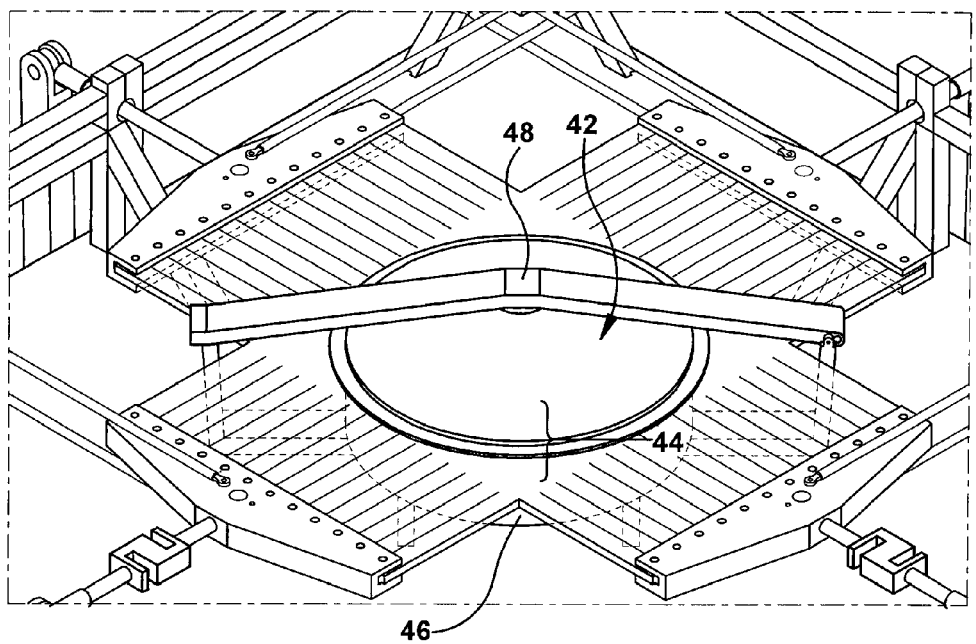
FIG. 4 is a diagram of an apparatus according to the invention with a gas permeability-testing chamber.

FIG. 4 depicts an apparatus according to the invention having a permeability chamber. In this FIG. 4, permeability test chamber top cover 42 and permeability test chamber bottom cover 46 cooperate to define a closed chamber 44. Clamp bar 48 is used to clamp the upper and lower portions of the permeability chamber together. More specifically chamber 44 provides a container in which the flexible, fabric laminate material being tested is horizontally mounted between top cover 42 and bottom cover 46. During testing, the test gas enters the bottom cover 46 through an inlet valve or mechanism (not shown). Chamber 44 may be in the vacuum state for testing. Top cover 42 includes an outlet valve or mechanism (not shown) to measure and remove permeate that has passed to the top cover 42 from the bottom cover 46 through the flexible, fabric laminate material.

Permeability test chamber bottom cover 46 may also function as a film adhesion or peel test chamber. In this capacity, the chamber 44 provides a container and interfaces for generating a volume of a known reference gas on one side of the flexible, fabric laminate material or sample fabric, which, as in the permeability test set-up, is placed horizontally between top cover 42 and bottom cover 46. It further provides a volume and interfaces, applied to the fabric surface opposite to that where the gas is applied, to apply a vacuum source. In use, this test is used to check and/or verify the adhesion of film material to reinforcements. For example, an alternative to the flexible, fabric laminate described hereinabove may be the addition thereto of stronger fibers to address known stress parameters or conditions. Such fibers may be included in the laminate in any amount so as to reinforce the laminate in response to an anticipated or potential stress under given conditions of use.

The apparatus of the subject invention allows various stress states to be tested, simultaneously, and without the need to apply forces in a symmetric manner, on a fabric sample. Advantageous to this system, in addition to the advantages mentioned above, is the capability to test samples in the cruciform form, which allows performance parameters to be assessed on samples having various sizes, all using the same apparatus. For example, slight modification of clamping mechanisms, linkages, load cells, and other components will allow use of one apparatus to test and evaluate samples in a range of sizes. This enhances not only the cost efficiency of the testing procedure, but also addresses sample preparation concerns. More importantly, because only one machine is being used, the data generated can more accurately be compared between test runs even if the sample sizes may vary.

Figure 5:
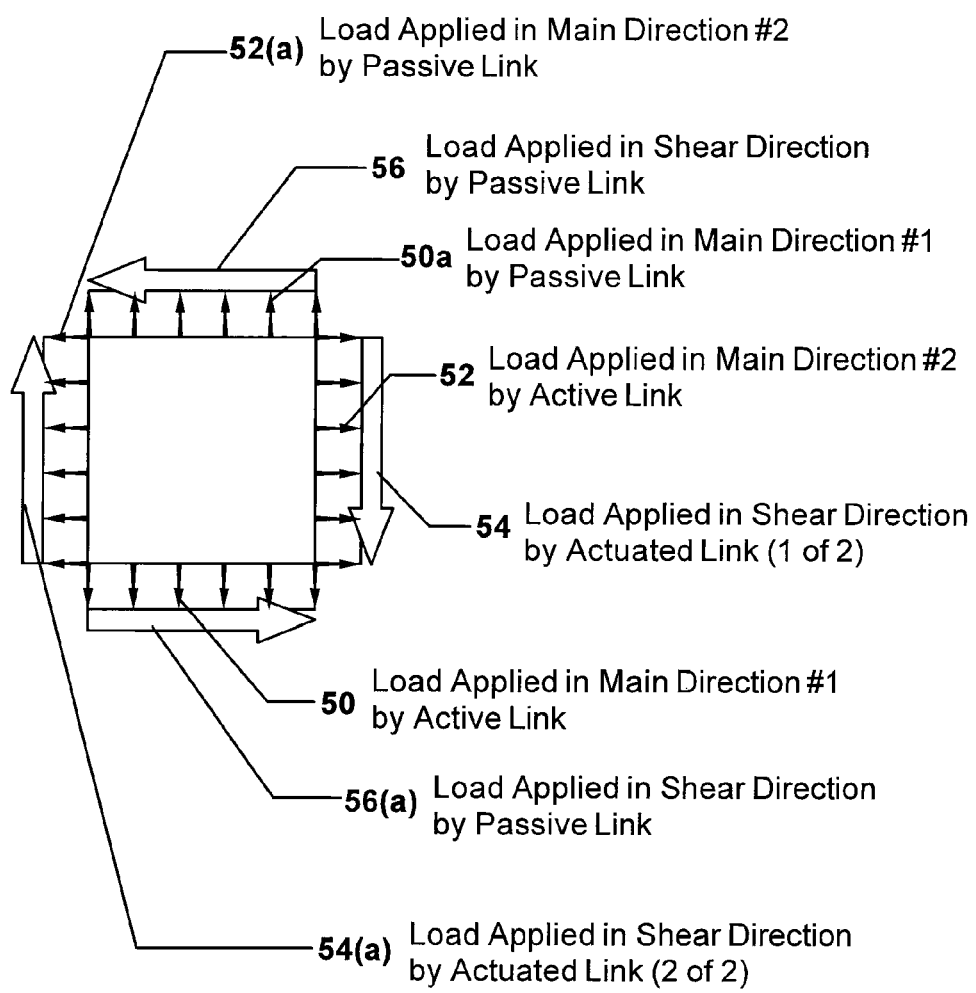
FIG. 5 is a diagram of a flexible, fabric laminate material sample showing various load applications.

FIG. 5 is a diagram of a flexible, fabric laminate material or sample fabric, in the noted cruciform shape, and an explanation of the loading capability of an apparatus according to the invention. In this FIG. 5, and with reference to the apparatus as shown in FIG. 1, load is applied in main orthogonal direction #1, shown by arrows 50, by the active primary load linkage 24. Opposite this load is the load applied in the main orthogonal direction #1, shown by arrows 50a, by passive primary load linkage 20. Likewise, load is applied in the main orthogonal direction #2, shown by arrows 52 and 52a, by the active and passive primary load linkages 24 and 20 respectively placed on these sides of the fabric. In addition to the foregoing, a simultaneous sheer stress is applied. The load applied on opposite sides or edges of the fabric will be the same, passive or active, though they will obviously exert force in opposite axial directions. Therefore, arrows 54 and 54*a* represent load applied in the sheer direction by a pair of actuated linkages 16, while arrows 56 and 56*a* represent load applied in the sheer direction by passive linkages 18.

In addition to the foregoing, the results of testing conducted using the apparatus and process herein is scalable and therefore readily applicable to many design applications. Further, the flat shape of the high strength flexible, fabric laminate sample allows for integration of auxiliary test scenarios. In this regard, the permeability and peel strength tests provide just two examples of such auxiliary testing, though others may be available. Because the loads are independently controlled, there is an unlimited combination of loading conditions which can be assessed, and cyclic and programmable loading profiles which may be applied to simulate any number of potential uses of the material, thus providing a mechanism to more accurately evaluate potential failure points of a specific material in a specific use situation or under specific conditions.

For example, cyclic loading is a repetitive and controlled loading of the sample. This type of loading is used to determine the behavior of a material as it experiences loading and unloading during day-to-day operational and cyclic use. This type of cyclic loading and unloading may also be generated by vibrations from the propulsion system.

The apparatus and process for using the same in accord with the invention provides valuable information for a multitude of potential material applications. Though the invention has been described herein with regard to certain aspects thereof, such aspects are not intended to limit the uses of the apparatus or process, which will find application in many related testing scenarios.

What we claim is:

1. An apparatus for testing the strength of a material under stress conditions comprising multiple load-generating mechanisms, each such mechanism being operable simultaneously with and independent of each other such mechanism, wherein each load-generating mechanism applies a force that simulates a stress condition in the form of at least one of strain, in-plane sheer, cyclic loading, gas permeability, and film or ply separation.

2. The apparatus of claim 1 wherein the material is flexible fabric laminate.

3. The apparatus of claim 1 wherein loads generated by the load-generating mechanisms are individually controlled.

4. The apparatus of claim 1 wherein the load-generating mechanisms include one main load-generating mechanism.

5. The apparatus of claim 4 wherein the main load-generating mechanisms simultaneously tests at least two orthogonal load ratios.

6. The apparatus of claim 5 wherein the at least two orthogonal load ratios are 1:1 and 1:2.

7. The apparatus of claim 1 wherein the apparatus further simultaneously tests in-plane sheer.

8. The apparatus of claim 3 wherein the loads are at least one of biaxial or uniaxial or a combination thereof.

9. The apparatus of claim 1 wherein the material is tested for permeability to at least one of nitrogen, air, helium or hydrogen, while the material is subjected to various combinations of at least two independent biaxial, in plane shear, cyclic or pressure loading conditions.

10. The apparatus of claim 1 wherein the material is tested for resistance to delamination and ply separation while the material is subjected to various combinations of at least two independent biaxial, in plane shear, cyclic or pressure loading conditions.

11. The apparatus of claim 1 wherein the apparatus creates a sheering moment by applying opposite balanced loads resulting in the creation of in-plane sheer.

12. The apparatus of claim 1 wherein the application of load is controlled by an external, programmable source.

13. The apparatus of claim 12 wherein the programmable source applies the load according to a cyclic program over a period of time.

14. A multiple load-generating apparatus for testing performance parameters of a material under stress, the apparatus comprising a system of load-bearing arms arranged around the perimeter of the apparatus, each arm contacting the material and adapted to individually and simultaneously apply force to the material, such that the material experiences at least two different stresses.

15. The apparatus of claim 14 wherein the apparatus tests at least two of strain, in-plane sheer, cyclic loading, gas permeability, and gas barrier film separation.

16. The apparatus of claim 14 wherein the apparatus simultaneously tests biaxial stress and in-plane sheer.

17. The apparatus of claim 14 including a chamber for testing the gas permeability parameters of the material.

18. A method for testing the performance parameters of a material under stress comprising:
   providing a material to be tested;
   positioning the material in a testing apparatus comprising a system of load-generating mechanisms arranged around the perimeter of the apparatus, each mechanism contacting the material and adapted to individually and simultaneously apply force to the material, such that the material experiences at least two different stresses;
   simultaneously applying at least two forces to the material from at least two different mechanisms of the apparatus;
   measuring the amount of force applied to the material; and
   using the measured force to predict the failure point of the material under stress.

19. The method of claim 18 wherein the material is a flexible fabric laminate.

20. The method of claim 18 wherein the force is a load applied to the material.

21. The method of claim 18 wherein the load-generating mechanisms include one main load-generating mechanism.

22. The method of claim 21 wherein the main load-generating mechanisms simultaneously tests at least two orthogonal load ratios.

23. The method of claim 22 wherein the at least two orthogonal load ratios are 1:1 and 1:2.

24. The method of claim 18 wherein the apparatus further simultaneously tests in-plane sheer.

25. The method of claim 18 wherein the force is at least one of a uniaxial load and independently controlled biaxial loads.

26. The method of claim 18 wherein the stress is in the form of in-plane shear.

27. The method of claim 18 wherein the stress is in the form of a uniaxial load, independently controlled biaxial loads, in-plane sheer and pressure loading, applied to the material simultaneously.

28. The method of claim 18 wherein the stress is in the form of gas pressurization.

29. The method of claim 18 wherein the stress is in the form of cyclic loading and unloading of force.

30. The method of claim 18 wherein the application of load is controlled by an external, programmable source.

* * * * *